United States Patent [19]

Vasta

[11] 4,368,309
[45] Jan. 11, 1983

[54] POLYMERS OF VINYL OXAZOLINE DRYING OIL ESTERS MADE BY AN IMPROVED PROCESS

[75] Inventor: Joseph A. Vasta, Wilmington, Del.

[73] Assignee: E. I. Du Pont de Nemours & Co., Wilmington, Del.

[21] Appl. No.: 328,844

[22] Filed: Dec. 9, 1981

Related U.S. Application Data

[63] Continuation-in-part of Ser. No. 211,584, Dec. 1, 1980, Pat. No. 4,340,741.

[51] Int. Cl.$^3$ ............................ C08L 1/10; C08L 1/14; C09D 3/74
[52] U.S. Cl. ..................................... 526/258; 548/237
[58] Field of Search ................. 526/258; 548/237, 239

[56] References Cited

U.S. PATENT DOCUMENTS

| | | | |
|---|---|---|---|
| 3,248,397 | 4/1966 | Purcell | 548/239 |
| 3,523,123 | 8/1970 | Wehrmeister | 548/237 |
| 3,553,124 | 1/1971 | Donatello et al. | 548/239 |
| 3,654,229 | 4/1972 | Hunsucker | 548/239 |
| 3,960,816 | 6/1976 | Jurisch | 524/95 |
| 4,147,674 | 4/1979 | Vasta | 428/334 |

FOREIGN PATENT DOCUMENTS 1134050 11/1968 United Kingdom .

OTHER PUBLICATIONS

Brochure Oxazolines by Commercial Solvents Corp. pp. 1-30 1969.

*Primary Examiner*—Ronald W. Griffin

[57] ABSTRACT

Polymers of vinyl oxazoline drying oil ester which esters are made by a process which reacts drying oil fatty acids with tris(hydroxy methyl) amino methane to form an intermediate which intermediate is further reacted at about 175°-195° C. with a formaldehyde/alcohol solution to form the vinyl oxazoline drying oil ester; the improvement used with this process is the use of at least 3 moles of formaldehyde to one mole of intermediate and about 1-5% by weight, based on the weight of the intermediate, of methanol and adding after the reaction with formaldehyde about 5-25% by weight, based on the weight of the ester solution, of an alcohol, a ketone or a mixture of an alcohol and a ketone; coating compositions of these polymers are also disclosed.

8 Claims, No Drawings

POLYMERS OF VINYL OXAZOLINE DRYING OIL ESTERS MADE BY AN IMPROVED PROCESS

CROSS REFERENCE TO RELATED APPLICATIONS

This application is a continuation-in-part application of Ser. No. 211,584 filed Dec. 1, 1980, now U.S. Pat. No. 4,340,741, issued July 20, 1982.

BACKGROUND OF THE INVENTION

This invention is related to a polymer containing vinyl oxazoline drying oil esters which esters are made by an improved process.

A process for preparing vinyl oxazoline drying oil esters is disclosed in Purcell U.S. Pat. No. 3,248,397 issued Apr. 26, 1966. The process as taught in the patent provides esters with a relatively low vinyl content. Dimers and oligomers of these esters also are formed in the process. These dimers and oligomers often cause gelation and seed formation in polymers formed with these esters. Polymers prepared with esters having a low vinyl content when formulated into coating compositions have a lower level of exterior durability and are subject to cracking. There is a need for an improved process that prepares vinyl oxazoline drying oil esters having a high vinyl level and do not contain dimers or oligomers.

SUMMARY OF THE INVENTION

A polymer of polymerized ethylenically unsaturated monomers and a vinyl oxazoline drying oil ester wherein the vinyl oxazoline drying oil ester is prepared by reacting at about 150°–225° C., in the presence of a solvent, drying oil fatty acids with tris(hydroxymethyl) amino methane to form an intermediate, the intermediate then is reacted at about 175°–190° C. with a formaldehyde alcohol solution to form a solution of a vinyl oxazoline drying oil ester of the formula

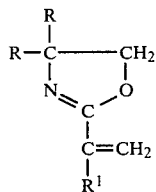

where R is

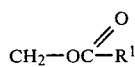

and $R^1$ is the residue of a drying oil fatty acid; the improvement that is used with the above process comprises the use of at least 3 moles of formaldehyde to one mole of intermediate and about 1–5% by weight, based on the weight of the intermediate, of methanol and adding after the reaction with formaldehyde about 5–25% by weight, based on the weight of the ester solution, of an alcohol having 1–6 carbon atoms, a ketone or a mixture of an alcohol and a ketone.

DESCRIPTION OF THE INVENTION

The improved process used in this invention forms a vinyl oxazoline drying oil ester in which at least 60% and preferably 80–100% of the esters have vinyl groups. Polymers made from these esters when formulated into coating compositions provide finishes with excellent outdoor durability in comparison to finishes formulated from such polymers that utilize vinyl oxazoline crying oil esters which have a low vinyl content.

In the process used in this invention oligomers and dimers of the vinyl oxazoline drying oil esters are not formed. Gelation and seed formation are not present to any substantial extent in polymers formulated from the vinyl oxazoline esters of the improved process.

In the improved process, an amino hydroxy compound such as tris(hydroxymethyl) amino methane is reacted with drying oil fatty acids in the presence of solvent at about 150°–225° C. for about 1–4 hours to form an intermediate of oxazoline drying oil ester.

Typical drying oil fatty acids are soya oil fatty acids, linseed oil fatty acids, tall oil fatty acids, tung oil fatty acids, safflower oil fatty acids, poppy seed oil fatty acids and the like. These acids contain mixtures of $C_{18}$ unsaturated fatty acids such as linoleic acid, linolenic acid and oleic acid. Other acids that can be used are dodecanoic acid, ricinoleic acid, licanic acid, arachidonic acid, behenic acid, erucic acid, clupanodonic acid, lignoceric acid and nisinic acid.

The oxazoline drying oil ester has the following formula:

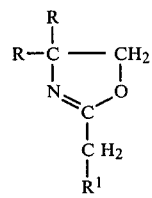

where R and $R^1$ are as defined above.

The improvement that is used with the above process to form esters in which at least 60% and preferably 80–100% of the esters contain a vinyl group is the reaction of the intermediate of the oxazoline drying oil ester with at least a 3/1 molar excess of formaldehyde to ester. Generally, about 3.2 to 4.0 moles of formaldehyde are used per mole of oxazoline drying oil ester. A formaldehyde methanol mixture is used. About 1–5% by weight, based on the intermediate, of methanol is used. Reaction temperature is the same as above and reaction time is about 1–5 hours. Preferably, a reaction temperature of 180°–190° C. is used to obtain a high conversion.

Formaldehyde compounds such as paraformaldehyde and formaldehyde releasing substances such as trioxane also can be used.

The presence of methanol in the reaction reduces and essentially eliminates any build-up of paraformaldehyde in a condenser used in the process for making the ester. The methanol either can be added with the formaldehyde or introduced into the top of a condenser used in the reaction.

After the reaction is complete, a solvent of alcohol having 1–6 carbon atoms, ketone or a mixture of the above is added to the vinyl oxazoline drying oil ester solution to cool the ester solution below 140° C. Below 140° C. no further reaction will occur. About 5–25% by weight, based on the weight of the ester solution, of the solvent is added. The solvent can be chilled to rapidly reduce the temperature of the solution.

Typical alcohols that can be used are methyl alcohol, butyl alcohol, isobutyl alcohol, pentyl alcohol, hexyl alcohol and the like. Typical ketones are acetone, methyl ethyl ketone, methyl isobutyl ketone, methyl amyl ketone and the like.

The cooling of the ester solution reduces the formation of dimers and oligomers of the vinyl oxazoline drying oil esters.

Vinyl oxazoline drying oil esters made according to the above process are readily polymerized with ethylenically unsaturated monomers as taught in Vasta U.S. Pat. No. 4,147,674 issued Apr. 3, 1979 which is incorporated by reference.

Typically ethylenically unsaturated polymerizable monomers that can be used are as follows: alkyl methacrylates and acrylates having 1-18 carbon atoms in the alkyl group such as methyl methacrylate ethyl methacrylate, propyl methacrylate, butyl methacrylate, pentyl methacrylate, hexyl methacrylate, octyl methacrylate, nonyl methacrylate, decyl methacrylate, lauryl methacrylate, stearyl methacrylate and the like; methyl acrylate, ethyl acrylate, propyl acrylate, butyl acrylate, pentyl acrylate, hexyl acrylate, octyl acrylate, nonyl acrylate, decyl acrylate, lauryl acrylate, stearyl acrylate and the like; hydroxy alkyl acrylates and methacrylates, hydroxy ethyl acrylate, hydroxy propyl acrylate, hydroxy butyl acrylate, hydroxy ethyl methacrylate, hydroxy propyl methacrylate, hydroxy butyl methacrylate and the like; ethylenically unsaturated carboxylic acids such as methacrylic acid, acrylic acid, maleic acid or its anhydride and the like; styrene; acrylonitrile, acrylamide, methacrylamide and mixtures of the above monomers.

Typical useful polymers which are used to form high quality coating compositions are as follows:

(1) a polymer of about 22-28% by weight of styrene, about 22-28% by weight methyl methacrylate, about 37-43% by weight of a vinyl oxazoline drying oil ester (described above) where R and $R^1$ are from soya oil fatty acids, about 3-7% by weight of lauryl methacrylate and about 3-7% by weight of acrylic acid;

(2) a polymer of about 22-28% by weight of styrene, about 22-28% by weight methyl methacrylate, about 37-43% by weight of a vinyl oxazoline drying oil ester (described above) where R and $R^1$ are from linseed oil fatty acids and about 8-12% by weight acrylic acid; or (3) a polymer of about 22-28% by weight of styrene, about 22-28% by weight methyl methacrylate, about 37-43% by weight of a vinyl oxazoline ester (described above) where R is from soya oil fatty acids and about 8-12% by weight of acrylic acid.

The following example illustrates the invention. All parts and percentages are on a weight basis unless otherwise indicated:

EXAMPLE I

An oxazoline drying oil ester is prepared by charging the following constituents into a reaction vessel equiped with a stirrer, reflux condenser, a heating mantle and a nitrogen inlet.

|  | Parts by Weight |
|---|---|
| Soya oil fatty acids | 835.00 |
| Tris(hydroxymethyl) amino methane | 129.30 |
| Toluene | 26.03 |
| Total | 990.33 |

The constituents are heated under a nitrogen blanket and distillate is removed as follows:

| Total Reaction Time (Min) | Temp. (°C.) | Distilllate Removed |
|---|---|---|
| 35 | 125 | — |
| 55 | 155 | 11.17 |
| 65 | 160 | 20.06 |
| 82 | 162 | 30.50 |
| 98 | 173 | 43.50 |
| 130 | 175 | 51.50 |
| 240 | 210 | 66.30 |
| 370 | 215 | 71.50 |
| 400 | 215 | 73.94 |

The resulting ester has an acid number of about 4.31.

A vinyl oxazoline drying oil ester then is prepared by charging the following constituents into a reaction vessel equipped as above:

|  | Parts by Weight |
|---|---|
| Portion 1 | |
| Drying oil oxazoline ester (prepared above) | 406.0 |
| Portion 2 | |
| Butyl Formcel (40% solution of formaldehyde in n-butanol) | 110.8 |
| Portion 3 | |
| Methyl alcohol | 24.8 |
| Total | 541.6 |

Portion 1 is charged into the reaction vessel and heated to about 185°-190° C. Portion 2 is added at a uniform rate over a 120 minute period. Simultaneously with portion 2, portion 3 is added at a uniform rate over a 165 minute period while maintaining the reaction temperature at about 185°-190° C. After the addition of portion 3, heat is turned off and the resulting composition is cooled to room temperature.

The composition contains 78% of nonvolatile solids oxazoline drying oil ester and has a relative viscosity measured at 25° C. of 1.019. Gel permeation chromatography (GPC) data indicates that about 90% of the esters have a vinyl group.

Polymer A is prepared using the same constituents and polymerization procedure as in Example 1 of U.S. Pat. No. 4,147,674 with the above prepared 90% oxazoline drying oil ester. White mill base A and white paint A are prepared from this polymer using the same constituents as in Example 1 of the above patent except polymer A is used. The resulting paint is sprayed onto phosphatized steel parts and dried at room temperature.

A vinyl oxazoline drying oil ester is prepared using the above constituents and reaction conditions except a 1:1 molar ratio of formaldehyde to drying oil oxazoline ester is used. The resulting composition has only about 30% of the ester containing vinyl groups as determined by GPC data.

Polymer B is prepared using the same constituents and polymerization procedure as in Example 1 of the above U.S. Pat. No. 4,147,674 with the above prepared 30% vinyl drying oil oxazoline ester. White mill base B and white paint B are prepared from this polymer using the same constituent as in Example 1 of the above patent except polymer B is used. The resulting paint is sprayed onto phosphatized steel panels and dried at room temperature.

The panels were exposed in Florida facing South at a 45 degree angle. The panels coated with paint A showed substantially less degradation from weathering than the panels coated with paint B. This is an expected result since paint A was formulated from a polymer containing a high vinyl content vinyl oxazoline drying oil ester.

I claim:

1. A polymer comprising polymerized ethylenically unsaturated monomers and a vinyl oxazoline drying oil ester; wherein the vinyl oxazoline drying oil is prepared by a process which comprises reacting at about 150°–225° C., in the presence of solvent, drying oil fatty acids with tris(hydroxymethyl) amino methane to form an intermediate, said intermediate being further reacted at about 175°–190° C. with a formaldehyde alcohol solution to form a solution of a vinyl oxazoline drying oil ester wherein at least 60% of the esters have vinyl groups and are of the formula

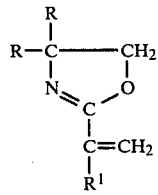

where R is

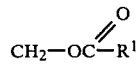

and $R^1$ is the residue of a drying oil fatty acid;

the improvement used therewith comprises the use of at least 3 moles of formaldehyde to one mole of intermediate and about 1–5% by weight, based on the weight of the intermediate, of methanol and adding after the reaction with formaldehyde about 5–25% by weight, based on the weight of the ester solution, of an alcohol having 1–6 carbon atoms, a ketone or a mixture of said alcohol and ketone.

2. The polymer of claim 1 in which the drying oil fatty acids of the ester are soya oil fatty acids.

3. The polymer of claim 1 in which the drying oil fatty acids of the ester are tall oil fatty acids.

4. The polymer of claim 1 in which the drying oil fatty acids of the ester are linseed oil fatty acids.

5. The Polymer of claim 1 in which the drying oil fatty acids of the ester comprise a mixture of linoleic acid, linolenic acid and oleic acid.

6. The polymer of claim 1 consisting essentially of polymerized monomers of about
    (a) 22–28% by weight, based on the weight of the polymer, of styrene,
    (b) 22–28% by weight, based on the weight of the polymer, of methyl methacrylate;
    (c) 37–43% by weight, based on the weight of the polymer, of the vinyl oxazoline ester of soya oil fatty acids,
    (d) 3–7% by weight, based on the weight of the polymer, of lauryl methacrylate; and
    (e) 3–7% by weight, based on the weight of the polymer, of acrylic acid.

7. The polymer of claim 1 consisting essentially of polymerized monomers of about
    (a) 22–28% by weight, based on the weight of the polymer, of styrene,
    (b) 22–28% by weight, based on the weight of the polymer, of methylmethacrylate,
    (c) 37–43% by weight, based on the weight of the polymer, of a vinyl oxazoline drying oil ester of linseed oil fatty acids and
    (d) 8–12% by weight, based on the weight of the polymer, of acrylic acid.

8. The polymer of claim 1 consisting essentially of polymerized monomers of about
    (a) 22–28% by weight, based on the weight of the polymer, of styrene,
    (b) 22–28% by weight, based on the weight of the polymer, of methyl methacrylate,
    (c) 37–43% by weight, based on the weight of the polymer, of a vinyl oxazoline drying oil ester of soya oil fatty acids and
    (d) 8–12% by weight, based on the weight of the polymer, of acrylic acid.

* * * * *